United States Patent [19]
Chida et al.

[11] Patent Number: 6,110,715
[45] Date of Patent: Aug. 29, 2000

[54] METHOD FOR PRODUCING ERYTHRITOL USING A MICROORGANISM

[75] Inventors: Saburo Chida, Kitamoto; Toshiro Ochiai, Kasukabe, both of Japan

[73] Assignee: Nikken Chemicals Co., Ltd., Tokyo, Japan

[21] Appl. No.: 09/194,890

[22] PCT Filed: May 15, 1997

[86] PCT No.: PCT/JP97/01640

§ 371 Date: Dec. 4, 1998

§ 102(e) Date: Dec. 4, 1998

[87] PCT Pub. No.: WO97/47760

PCT Pub. Date: Dec. 18, 1997

[30] Foreign Application Priority Data

Jun. 13, 1996 [JP] Japan .................................... 8-172806

[51] Int. Cl.[7] ........................................................ C12P 7/18
[52] U.S. Cl. ........................ 435/158; 435/171; 435/254.1; 435/911
[58] Field of Search ............................... 435/158, 254.1, 435/171, 911

[56] References Cited

FOREIGN PATENT DOCUMENTS 9-154589   6/1997   Japan .

OTHER PUBLICATIONS

Japan Abstract 09154589 Published Jun. 17, 1997 Makoto Et Al "Production of Erythritol" Mitsubishi Chem Corp.

Aoki et al, "Microbial Transformation of Sucrose and Glucose to Erythritol", *Biotechnology Letters*, vol. 15, No. 4, pp. 383–388 (Apr. 1993).

Inglis et al, "*Trichosporonoides megachiliensis*", *Mycologia*, vol. 84, No. 4, pp. 555–570 (1992).

*Primary Examiner*—Herbert J. Lilling
*Attorney, Agent, or Firm*—Fishauf, Holtz, Goodman, Langer & Chick, P.C.

[57] ABSTRACT

The present invention provides a method for producing erythritol comprising cultivating microorganisms, which produce erythritol, belonging to *Trichosporonoides megachiliensis* in a culture medium having a high saccharide concentration and then recovering the erythritol accumulated in the culture medium. According to the present invention, cultivation period for producing erythritol can be shortened remarkably, and saccharide-based erythritol yield is excellent. Moreover, a large amount of erythritol can be produced efficiently, without much cost, since the same effect can be confirmed in case of using a culture medium at high saccharide concentration.

19 Claims, No Drawings

METHOD FOR PRODUCING ERYTHRITOL USING A MICROORGANISM

TECHNICAL FIELD

The present invention relates to a method for producing erythritol using microorganisms and more precisely to a method for producing erythritol using strains belonging to *Trichosporonoides megachiliensis*.

BACKGROUND ART

Two microorganisms, namely, *Moniliella tomentosa* var. *pollinis* CBS461.67 and *Aureobasidium* sp. SN-G42 FERM P-8940, are known currently to be employed practically to produce erythritol.

The former is employed, for example, in methods for producing polyols in an industrial scale by means of fermentation of saccharides (Japanese Patent Publication No. 6-30591 (30591/1994), ibid 6-30592 (30592/1994), ibid. 6-30593 (30593/1994), ibid 6-30594 (30594/1994)), and in these publications methods for producing a series of polyols including erythritol are disclosed.

On the other hand, the latter is disclosed in Japanese Patent Publications 4-11189 (11189/1992) and ibid 4-635 (635/1992) in which a novel microorganism having an erythritol producing ability and a method for producing erythritol by means of fermentation using such microorganism are described.

Meanwhile, a microorganism belonging to genus Trichosporonoides was reported by Marina A. Y. Aoki et al. of the State University of Campinus in Brazil (Biotechnology Letters, Volume 15, No.4, p. 383–388, April 1993) to be employed in conversion from sucrose and glucose to erythritol, although the species is not known. According to this report, the rates of conversion from glucose to erythritol and sucrose to erythritol were as relatively high as 43.0% and 37.4%, respectively, but the saccharide concentration for such yields was as low as 10 w/v % and the cultivation thereof takes as many days as six days, indicating a poor applicability to a production in an industrial scale.

*Trichosporonoides megachiliensis* employed in the present invention was reported to be a new strain by G. Douglas Inglis and Lynne Sigler of the University of Alberta in Canada (Mycologia, Volume 84, No. 4, p. 555–570, 1992). Their report contained description of morphological and physiological characteristics of a strain identified as a new strain but no description of its ability of producing erythritol.

We, the present inventors, have studied the method for producing erythritol with a use of microorganisms and finally found that *Trichosporonoides megachiliensis* converted saccharaides such as glucose to erythritol effectively with a high yield and completed the present invention.

DISCLOSURE OF THE INVENTION

An object of the present invention is to provide a method for producing erythritol by culturing a strain belonging to *Trichosporonoides megailiensis* in a medium containing saccharide at high concentration, especially at a concentration of 20–50 w/v % and recovering erythritol from culture fluid.

The present invention relates to a method for producing erythritol comprising cultivating a strain of *Trichosporonoides megachiliensis* in a culture medium at high saccharide concentration and then recovering the erythritol accumulated in the culture medium.

PREFERRED EMBODIMENT OF THE INVENTION

Examples of the strains belonging to *Trichosporonoides megachiliensis* employed in the present invention are *Trichosporonoides megachiliensis* CBS 190.92 strain (UAMH 6490), *Trichosporonoides megachiliensis* CBS 191.92 strain (UAMH 6822) as well as those strains reported by G. Douglas Inglis et al. of the University of Alberta in Canada such as *Trichosporonoides megachiliensis* UAMH 6820 strain, *Trichosporonoides megachiliensis* UAMH 6821 strain, *Trichosporonoides megachiliensis* UAMH 6823 strain (these strains are stored at the University of Alberta Microfungus Collection and Herbarium) etc. and the variant obtained by treating those strains by a standard mutating method, such as physical mutating methods such as ultra-violet irradiation and radioactive irradiation as well as chemical mutating methods using chemical mutating agents such as ethyl methanesulfonic acid, nitrosoguanidine, etc.

The strain is cultivated aerobically in a liquid medium containing carbon source, nitrogen source, inorganic salts, etc.

The carbon source may be saccharides such as glucose, fructose, sucrose and maltose and starch-saccharified liquor containing these saccharides as well as carbohydrates such as sweet potato syrup and beet syrup, which may be employed independently or in combination. Among them glucose, fructose and sucrose can be used preferably.

The nitrogen source may be nitrogen compounds capable of being utilized by said microorganism, such as yeast extract, peptone, malt extract, corn steep liquor, aqueous ammonia, ammonium salts, urea, nitrates, which may be employed independently or in combination.

The inorganic salts may be phosphates, magnesium salts, calcium salts, potassium salts, iron salts, manganese salts and the like.

In addition, in order to restrain any foam in the culture medium, defoaming agents such as silicone resin ordinary used can be optionally used.

The cultivation is conducted by inoculating a liquid medium containing saccharides at a high concentration, preferably at 20 to 50 w/v %, more preferably at 30 to 40 w/v % and other nutrient sources as described above directly with the strain or with a seed inoculant culture obtained by pre-incubation followed by cultivation usually at pH 3 to 8, preferably at 3 to 6, at a temperature of 24 to 40° C., preferably at 35 to 38° C., usually for a period of 3 to 8 days. Preferably, the cultivation is terminated at a time point when the maximum utilization of the nutrient sources in the medium and the maximum production of erythritol in the culture medium are achieved.

Erythritol accumulated in the culture medium is separated and recovered from the culture medium by a standard manner. For example, the cells are removed from the culture medium by filtration or centrifugation and then the culture fluid is subjected to an appropriate combination of ion exchange resin treatment, adsorption chromatography, solvent extraction, concentration, crystallization and the like. In addition, decoloration with activated carbon and recrystallization employed usually may also be conducted for the purpose of removing impurities.

The present invention is further illustrated in the following examples.

EXAMPLE 1

Cultivation Temperature and Yield of Erythritol

*Trichosporonoides megachiliensis* CBS 190.92 strain and CBS 191.92 strain were respectively inoculated to an yeast extract medium (containing 30 w/v % of glucose and 1 w/v % of yeast extract) and cultivated at 35° C. for 3 days while shaking. The culture fluid obtained was added at the concentration of 2% based on the medium to a L-shaped incubation tube in which the same yeast extract medium has previously been dispensed and incubated while shaking at 60 rpm at a temperature of 24.5 to 39.7° C. for 4 days using a temperature gradient shaker incubator (Advantec Toyo Co. Ltd., Model TN-2148).

The saccharide-based erythritol yield (yeild of produced erythritol against consumed glucose) was calculated by determining the amounts of remaining glucose and erythritol produced in the culture fluid using high performance liquid chromatography. The results are shown in Table 1.

TABLE 1

Saccharide-based erythritol yield

| Cultivation temperature (° C.) | *CBS 190.92 (%) | CBS 191.92 (%) |
|---|---|---|
| 24.5 | 21.0 | 17.4 |
| 25.5 | 21.9 | 16.6 |
| 27.0 | 22.4 | 21.3 |
| 28.5 | 23.1 | 21.9 |
| 30.1 | 22.8 | 22.4 |
| 31.5 | 22.9 | 24.1 |
| 33.2 | 23.2 | 24.5 |
| 35.0 | 23.3 | 27.8 |
| 36.5 | 28.1 | 28.0 |
| 38.0 | 29.4 | 28.8 |
| 39.7 | 21.0 | 17.9 |

*CBS: Centraal Bureau voor Schimmelcultures, Oosterstraat 1, P. O. Box 273, NL-3740 AG Baarn, The Netherlands As shown in Table 1, the optimum temperature range for erythritol production in CBS 190.92 strain was 36.5 to 38° C., with the saccharide-based erythritol yield being 28.1 to 29.4%. In contrast, the optimum temperature range for erythritol production in CBS 191.92 strain was 35 to 38° C., with the saccharide-based erythriol yield being 27.8 to 28.8%.

EXAMPLE 2

Effect of Types of Saccharides

An yeast extract medium was used as a basal medium while being supplemented with other saccharides (fructose, maltose and sucrose) instead of glucose and *Trichosporonoides megachiliensis* CBS 190.92 strain and CBS 191.92 strain were cultured. That is, each strain was inoculated to an yeast extract medium (containing 30 w/v % of glucose and 1 w/v % of yeast extract) and cultivated at 35° C. for 3 days while shaking. Then, the culture fluid obtained was inoculated (at the concentration of 2.0% based on the medium) as a seed to a modified yeast extract medium formulated by adding each saccharide to an yeast extract medium as a basal medium (containing 40 w/v % of saccharide and 1.33 w/v % of yeast extract) and the shaking culture in a conical flask was continued at 37° C. for 7 days. The results are shown in Table 2.

As evident from Table 2, the strains produced erythritol in the largest amounts, similar to glucose, when fructose and sucrose were employed as a carbon source of the medium.

TABLE 2

Amounts of produced erythritol

| Name of saccharide | CBS 190.92 (g/L) | CBS 191.92 (g/L) |
|---|---|---|
| Fructose | 102.7 | 93.2 |
| Maltose | 37.9 | 28.4 |
| Sucrose | 134.9 | 124.4 |

EXAMPLE 3

Effect of PH

*Trichosporonoides megachiliensis* CBS 190.92 strain and CBS 191.92 strain were respectively cultivated in media having different pH to examine effect of pH in production of erythritol. That is, each strain was inoculated to an yeast extract medium (containing 30 w/v % of glucose and 1 w/v % of yeast extract), which was then cultivated at 35° C. for 3 days while shaking. Subsequently, each strain was inoculated (1.0% based on the medium) to each medium (containing 40 w/v % of glucose and 1.33 w/v % of yeast extract) respectively adjusted to pH 2.5, 3.0, 4.0, 5.0, 6.0, 8.0 and 10.0 with hydrochloric acid and sodium hydroxide. During the cultivation, the pH of each medium was kept at the initial pH and cultivated in a conical flask at 37° C. for 5 days while shaking. After the cultivation, saccharide-based erythritol yield was calculated. The results are shown in Table 3.

TABLE 3

Saccharide-based erythritol yield

| pH | CBS 190.92 (%) | CBS 191.92 (%) |
|---|---|---|
| 2.5 | 23.6 | trace |
| 3.0 | 28.9 | 26.0 |
| 4.0 | 26.0 | 25.0 |
| 5.0 | 27.1 | 24.6 |
| 6.0 | 26.2 | 24.7 |
| 8.0 | 27.2 | 26.5 |
| 10.0 | 0 | 0 |

As evident from the table, in both strains erythritol can be produced stably within the wide range of pH from 3.0 to 8.0.

EXAMPLE 4

Saccharide Concentration and Cultivation Period

*Trichosporonoides megachiliensis* CBS 190.92 strain and CBS 191.92 strain were inoculated to an yeast extract medium (containing 30 w/v % glucose and 1 w/v % of yeast extract) and cultivated at 35° C. for 3 days while shaking. Then, the culture fluid obtained was added (at the concentration of 2% based on the medium) as a seed to saccharide concentration test media, i.e., yeast extract media whose glucose concentration has been respectively adjusted to 10, 20, 30, 40, 50 and 60 w/v % and cultivated in a conical flask at 37° C. while shaking. The cultivation was terminated at the time point when the highest (saccharide-based) erythritol yield was obtained. The results are shown in Table 4.

TABLE 4

|  | CBS 190.92 | | CBS 191.92 | |
| --- | --- | --- | --- | --- |
| Glucose concentration (w/v %) | Cultivation days | Saccharide-based erythritol yield (%) | Cultivation days | Saccharide-based erythritol yield (%) |
| 10 | 2 | 36.7 | 2 | 37.0 |
| 20 | 5 | 33.2 | 5 | 29.3 |
| 30 | 5 | 30.5 | 5 | 28.7 |
| 40 | 6 | 27.3 | 6 | 26.1 |
| 50 | 8 | 19.0 | 11 | 18.3 |
| 60 | 8 | 7.1 | 11 | 5.6 |

As shown in the table, at glucose concentration of 10 w/v %, cultivation of both CBS 190.92 strain and CBS 191.92 strain was terminated in rather short days as 2 days. At the end of the cultivation, saccharide-based erythritol yield was 36.7% and 37.0%, respectively.

While at saccharide concentration of 40 w/v %, cultivation of CBS 190.92 strain took 6 days with saccharide-based erythritol yield being 27.3%. The cultivation of CBS 191.92 strain took 6 days with saccharide-based erythritol yield being 26.1%.

EXAMPLE 5

Trichosporonoides megachiliensis strain (CBS 190.92) was inoculated to an yeast extract medium (containing 30 w/v % of glucose and 1 w/v % of yeast extract), which was then cultivated at 37° C. for 3 days while shaking. Subsequently, the culture fluid obtained was inoculated (2.0% based on the medium) to said yeast extract medium as a seed and cultivated in a mini-jar fermenter (Able Co. Ltd, Model DPC-2) at 37° C. for 5 days while stirring at 450 rpm. At the end of the cultivation, saccharide-based erythritol yield was 35.1%.

EXAMPLE 6

Part of the culture fluid of Example 4 cultivated in the medium containing 30 w/v % of glucose was employed to obtain a crystal of erythritol and the substance was then confirmed to be erythritol or not.

The culture fluid was filtrated to remove the cell to obtain supernatant. Then the supernatant obtained was subjected to decoloration with activated carbon and desalting on an ion exchange resin (SK-1B Mitsubishi Chemical Co. Ltd.); PA-408 Mitsubishi Chemical Co. Ltd.)) to obtain an effluent, which was concentrated to a saccharide concentration of 50% or higher and then cooled slowly to yield a crystal. Further, the crystal was conducted to recrystallization from water to obtain a crystal. IR absorption spectrum, melting point and nuclear magnetic resonance spectrum of the crystal obtained were compared with those of a standard erythritol, and were found to be identical, thus confirming the substance as erythritol.

INDUSTRIAL APPLICABILITY

With a use of strain belonging to Trichosporonoides megachiliensis in the method for producing erythritol of the present invention, cultivation period for production of erythritol can be quite short (according to a prior art, at saccharide concentration of 10%, cultivation takes 6 days while in the present invention cultivation is terminated within 2 days), compared with other well-known strains belonging to genus Trichosporonoides and moreover, the yield therebetween are almost the same. Therefore, the present invention is a quite efficient method for produicng erythritol.

Further, in the present invention, even when a medium of high saccharide concentration like 30 w/v % is used, the cultivation can be terminated in 5 days with rather high saccharide-based erythritol yield so that according to the method of present invention, it is possible to produce erythritol effectively at low cost.

What is claimed is:

1. A method for producing erythritol comprising cultivating a strain of Trichosporonoides megachiliensis in a culture medium at a saccharide concentration of 20–50 w/v% and then recovering the erythritol accumulated in the culture medium.

2. The method according to claim 1, wherein the saccharide concentration of the culture medium is 30–40 w/v/%.

3. The method according to claim 1, wherein the strain of Trichosporonoides megachiliensis is Trichosporonoides megachiliensis CBS 190.92 or Trichosporonoides megachiliensis CBS 191.92.

4. The method according to claim 1, wherein the saccharide is glucose, fructose or sucrose or mixture thereof.

5. The method according to claim 2, wherein the strain of Trichosporonoides megachiliensis is Trichosporonoides megachiliensis CBS 190.92.

6. The method according to claim 2, wherein the strain of Trichosporonoides megachiliensis is Trichosporonoides megachiliensis CBS 191.92.

7. The method according to claim 5, wherein the saccharide is glucose.

8. The method according to claim 6, wherein the saccharide is glucose.

9. The method according to claim 5, wherein the saccharide is sucrose.

10. The method according to claim 6, wherein the saccharide is sucrose.

11. The method according to claim 5, wherein the saccharide is fructose.

12. The method according to claim 6, wherein the saccharide is fructose.

13. The method according to claim 2, wherein the cultivating is carried out at a pH of 3 to 8.

14. The method of claim 13, wherein the pH is 3 to 6.

15. The method of claim 14, wherein the cultivating is carried out at a temperature of 24 to 40° C.

16. The method of claim 15, wherein the temperature is 35 to 38° C.

17. The method of claim 16, wherein the cultivating is carried out for 3 to 8 days.

18. The method of claim 17, wherein the strain of Trichosporonoides megachiliensis is Trichosporonoides megachiliensis CBS 190.92.

19. The method of claim 17, wherein the strain of Trichosporonoides megachiliensis is Trichosporonoides megachiliensis CBS 191.92.

* * * * *